United States Patent
Sliwa et al.

(10) Patent No.: US 6,368,275 B1
(45) Date of Patent: Apr. 9, 2002

(54) METHOD AND APPARATUS FOR DIAGNOSTIC MEDICAL INFORMATION GATHERING, HYPERTHERMIA TREATMENT, OR DIRECTED GENE THERAPY

(75) Inventors: John W. Sliwa, Los Altos, CA (US); William R. Dreschel, State College, PA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/414,235

(22) Filed: Oct. 7, 1999

(51) Int. Cl.⁷ .............................. A61B 8/00; A61B 8/12
(52) U.S. Cl. ....................... 600/437; 600/458; 600/302; 600/549
(58) Field of Search ................................. 600/437–438, 600/485–486, 488, 458, 549, 302; 73/570, 573–574, 579; 374/100, 117; 601/3

(56) References Cited

U.S. PATENT DOCUMENTS

| | | | |
|---|---|---|---|
| 4,021,364 A | | 5/1977 | Speiser et al. |
| 4,793,825 A | * | 12/1988 | Benjamin et al. ........... 600/438 |
| 5,475,318 A | * | 12/1995 | Marcus et al. ............... 324/762 |
| 5,492,122 A | | 2/1996 | Button et al. |
| 5,657,760 A | | 8/1997 | Ying et al. |
| 5,749,364 A | | 5/1998 | Sliwa, Jr. et al. |
| 5,779,643 A | * | 7/1998 | Lum et al. ..................... 600/462 |
| 5,863,520 A | | 1/1999 | Bichon et al. |
| 5,909,078 A | * | 6/1999 | Wood et al. ................. 310/307 |
| 5,914,507 A | * | 6/1999 | Polla et al. .................. 257/254 |
| 5,944,717 A | * | 8/1999 | Lee et al. ...................... 606/48 |
| 5,989,190 A | * | 11/1999 | Kaplan ........................ 600/438 |
| 6,092,530 A | * | 7/2000 | Weissman et al. .......... 128/899 |
| 6,287,765 B1 | * | 9/2001 | Cubiciotti |
| 6,291,140 B1 | * | 9/2001 | Andreoli et al. ............. 430/322 |

OTHER PUBLICATIONS

J. Bates, http://www.ssd.ornl.gov/BatteryWeb/default.htm, Thin–Film Rechargeable Lithium and Lithium–Ion Battries, Sep. 1998, p. 1.
Rodney M. LaFoliefte, http://quark.plk.af.mil/abstracts/97/TR971017.html; Microscopic Batteries for Use in Micro–Electromechanical Systems; Dec. 1996; p. 1.
http://www.atp.nist.gov/www/comps/briefs/98010039.html; The BioBattery™ Technology: An Innovative Medical Treatment for Arrhythmia; Oct. 1998; pp. 1–2.
http://mems.isi.edu/mems/materials/materials.cg; MEMS Material Database: Materials; pp. 1–7.
http://www.mds.nordion.com/business/products/monograph.html; TheraSphere® Yttrium–90 Glass Microspheres; pp. 1–9.
Theragenics Corporation; http://www.theragenics.com/about3.html; So What is Interstitial Radiation, and How Does it Work; pp. 1–3.
http://www.csa.com/hottopics/bceram.biblio09.html; Preparation, characterization, and in vitro release of ibuprofen from A1 sub 2 0 sub 3/PLA/PMMA composites; p. 1.
http://www.missouri.edu./–murrwww/biomed2.htm; More About the MURR Biomedical Program; pp. 1–3.

(List continued on next page.)

*Primary Examiner*—Francis J. Jaworski
(74) *Attorney, Agent, or Firm*—Brinks Hofer Gilson & Lione

(57) ABSTRACT

A micro-instrument suitable for property imaging in a body is less than one millimeter in each dimension. The micro-instrument includes a base having a first wall and a second wall, the second wall substantially circumscribing the first wall, and a lid connected with the base to form a cavity and the lid being temporarily deformable. Optionally, the lid can include a cantilever that is deformable. Also optionally, an electronic circuit can be attached with the micro-instrument. The micro-instrument can also be substantially spherical. An observable property of the micro-instrument varies as a function of a physiological property of the body.

40 Claims, 4 Drawing Sheets

OTHER PUBLICATIONS

Robert A. Day; http://www.ndt.net/article/rocky./rocky.htm; PVDF and Array Transducers; Sep. 1996; pp. 1–9.

Igal Ladabaum; Surface Micromachined Capacitive Ultrasonic Transducers; vol. 45, No. 3, May 3, 1998; pp. 678–690.

H. T. Soh et al., Silicon Micromachined Ultrasonic Immersion Transducers; Dec. 9, 1996; pp. 3674–3676.

Jacco A. De Zwart; Fast Magnetic–Resonance Temperature Imaging; Apr. 29, 1996; pp. 86–90.

Denis Le Bihan, MD, PhD; Temperature Mapping with MR Imaging of Molecular Diffusion: Application of Hyperthermia; Jun. 1989; pp. 853–857.

Kagayaki Kuroda; Temperature Mapping Using the Water Proton Chemical Shift: A Chemical Shift Selective Phase Mapping Method; 1997; pp. 845–851.

* cited by examiner

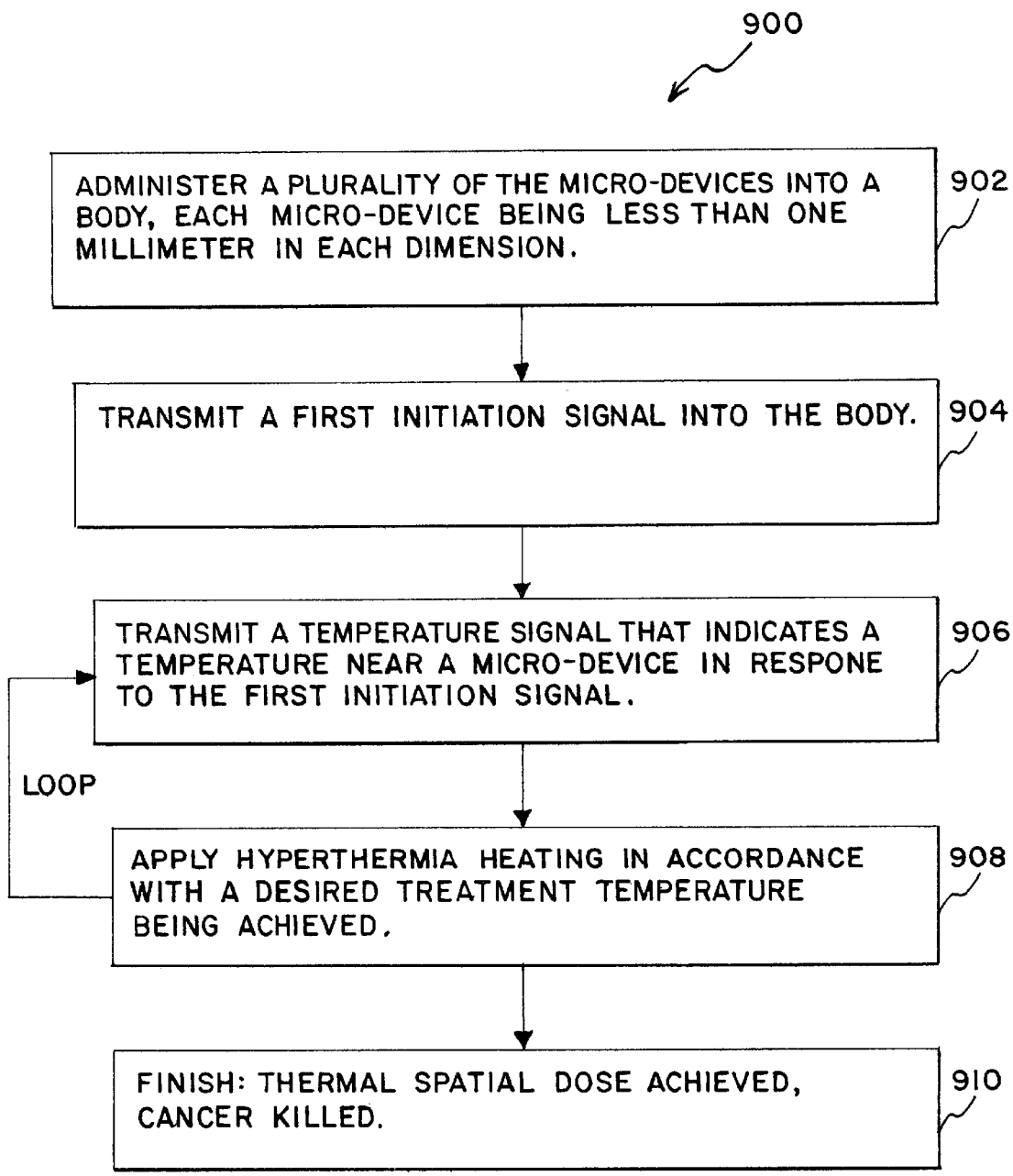

METHOD AND APPARATUS FOR DIAGNOSTIC MEDICAL INFORMATION GATHERING, HYPERTHERMIA TREATMENT, OR DIRECTED GENE THERAPY

BACKGROUND OF THE INVENTION

Currently, clinically useful systems for mapping body characteristics, such as temperature or pressure within the human body, provide only crude resolution. Invasive methods, including the use of catheters, often require hospitalization, gather data slowly or are expensive. U.S. Pat. No. 5,749,364 entitled "Method and Apparatus for Mapping Pressure and Tissue Properties" describes the use of contrast-agent micro-bubbles to image a body characteristic. The contrast agent's acoustic spectral behavior can be related to ambient pressure, as imposed, for example, by the pumping heart and surrounding blood. These approaches have limited accuracy. The data varies as a function of the variation in the properties of the contrast agent microbubbles. Such properties include composition, mean size, mean stiffness, etc. For example, their size varies—7 microns diameter plus or minus 3 microns (2 sigma). The contrast agent's material properties are difficult to control. Further the amount of information available from the contrast agent is limited.

Radio frequency ("RF") identity-card devices and micro-tags can be inserted under the skin of a pet. These tags currently merely transmit an identification signal that uniquely identifies the animal. They are too large to be used for measuring parameters throughout a tissue volume such as temperature or pressure.

BRIEF SUMMARY

Micro-instruments suitable for medical diagnostic imaging of body parameters are provided. Each micro-instrument has an observable property that varies as a function of a physiological property, such as temperature or pressure. For example, the observable property comprises an identifiable acoustic response. Based on the acoustic response, an image, a quantity or a combination thereof is generated.

In a first aspect, a micro-mechanical device for admission into a body and for communicating medical diagnostic information is improved. The improvement comprises a leadless micro-instrument particle having an observable property that varies as a function of a physiological property.

In a second aspect, a medical diagnostic ultrasound system for observing a physiological property of a body is provided. The system includes a transmit beamformer operable to transmit ultrasonic energy into the body. A micro-instrument particle has an observable property responsive to the ultrasonic energy where the observable property varies as a function of the physiological property of the body.

In other aspects, methods of use of a micro-instrument particle having an observable property that varies as a function of a physiological property are provided.

BRIEF DESCRIPTION OF THE DRAWINGS

The present invention is described with reference to the accompanying figures. In the figures, like reference numbers indicate identical or functionally similar elements.

FIG. 8 is flow diagram of a method for using the micro-instrument of FIGS. 1–4 for hyperthermia temperature-monitoring.

DETAILED DESCRIPTION OF THE PREFERRED EMBODIMENTS

Figure 1:
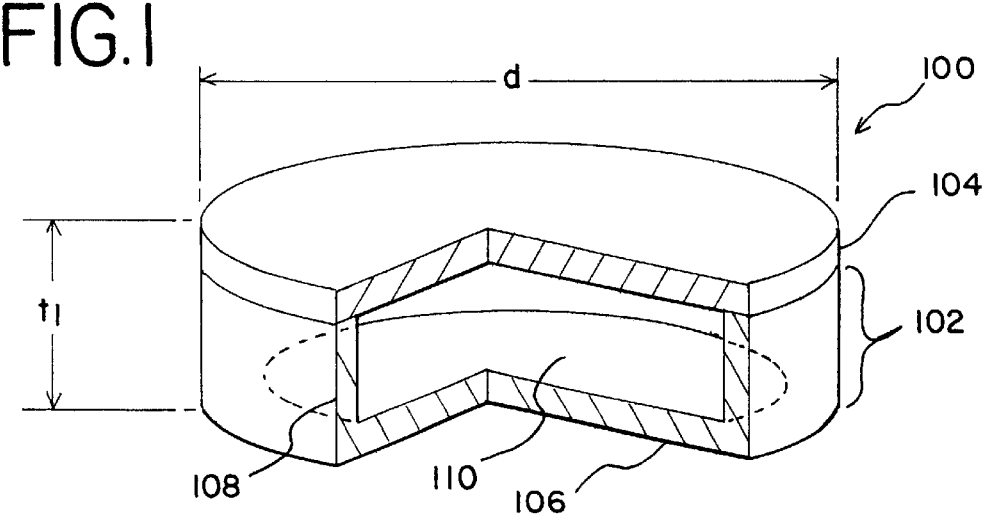
FIG. 1 is an isometric view of a micro-instrument with a cut-out showing the interior of the micro-instrument.

Magnetic resonance imaging ("MRI") and ultrasound may be used to measure or map temperature in the human body. Ultrasound has also been used to map pressure in the body. With MRI, a thermally sensitive contrast agent has been demonstrated. Pressure information, such as ultrasound-derived blood pressures in the heart's chambers, may allow cardiologists to better assess the health and performance of the cardiovascular system. Temperature monitoring using either MRI or ultrasound on a fine scale may be extremely useful for the control of a variety of tissue-heating or cooling therapies designed to kill cancer, such as hyperthermia as done by ultrasound, microwave or RF heating of targeted tissue. A real-time (e.g. several samples per second) temperature mapping capability may aid in these and other developing treatments.

Accurate temperature and/or pressure mapping is provided by a group of particles, each being a leadless micro-instrument, that behave similarly to provide information on a desired parameter. As used herein, leadless comprises no leads from the micro-instrument in the body to any point external of the body. A leadlesss micro-instrument may include electrical leads within the self-contained instrument. Each micro-instrument particle includes a micro-machined, micro-replicated or otherwise precision micro-shaped element capable of providing information representing a physiological property of a body. The micro-instrument is specifically engineered to vary an observable property as a function of the value of the selected physiological property being measured. Unlike conventional contrast-agent particles or micro-bubbles, the manufacturing processes herein shape each micro-instrument by a lithography, pattern transfer etching or a micro-replication process. Micro-replication comprises micro-molding, micro-stamping or micro pattern-transfer via a lithographic technique. Like conventional chemically derived contrast agents, the micro-instruments may be injected into the bloodstream or into tissue in any amount which is safe.

The micro-instrument particles are made using micromachining or micro-electro-mechanical systems ("MEMS") techniques. The micro-instrument 100 features are micro-machined or otherwise microformed by using microlithography and wet or dry etching interleaved with depositions. For example, acoustically resonant or deformable structures responsive to temperature are made. The deformable structures vary in a reproducible and predictable way with temperature, pressure, and/or other physiological properties. Batch processing of the micro-instruments, on a silicon wafer for example, allows large quantities of substantially identical microscopic devices to be made very cheaply.

The micro-instruments 100 are fabricated from materials such as silicon, silicon dioxide, silica glasses, nitrides, thin-film metals or other materials, such as are currently used in semiconductor manufacturing and MEMS. The micro-instruments 100 made of such materials may or may not be biodegradable. For some materials the micro-instrument 100 is rendered biocompatible by coating with a biocompatible coating, such as titanium, polyethylene, parylene or other biological coatings known to be biocompatible.

Micro-instruments 100 particularly those without electronic circuitry or other electronic elements, may be fabricated using materials such as glasses that slowly dissolve. Such slow dissolving glasses are used in radioactive seed implants. Alternatively, salt crystals that are ultimately absorbed in the bloodstream are used.

The micro-instruments are manufactured to provide an observable characteristic through mechanical (e.g., acoustic) and/or electrical mechanisms. Referring to FIG. 1, a micro-instrument for providing an acoustic response through a mechanical acoustic mechanism is shown. For example, a response signal indicative of the property being measured is transmitted (or returned) from the micro-instrument 100. The response signal contains data relating or relatable to bodily parameters. When the response signal is initiated at the micro-instrument 100 an incoming initiation signal is not required to obtain the bodily parameter information. Alternatively, the observable property is initiated responsive to externally created energy. For example, external insonification or RF radiation is transmitted into the body toward the microinstrument, and energy is indirectly or directly reradiated by the micro-instrument 100. Regardless of the source of the energy, the observable property contains information relating to one or more desired local physiological parameters and is contained in the response or signature of the microinstrument(s).

Figure 2:
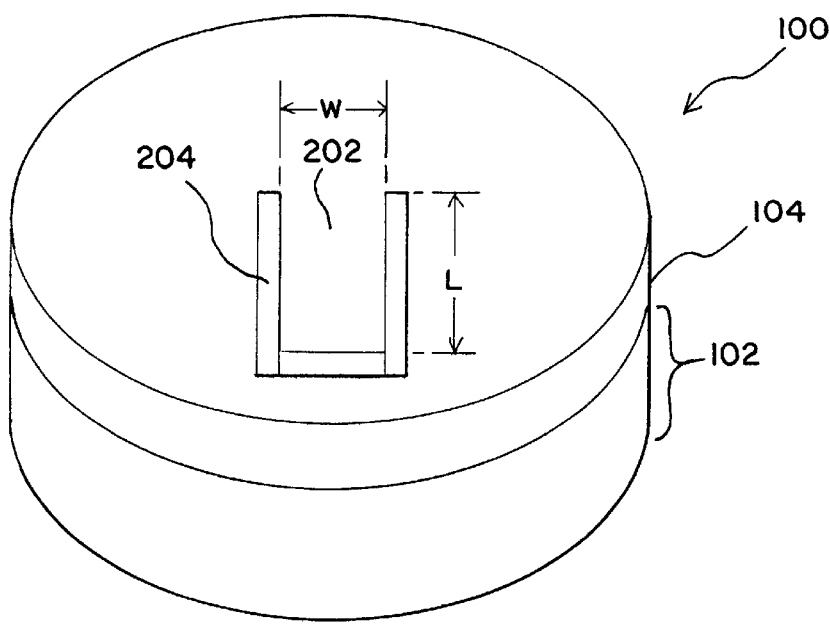
FIG. 2 is an isometric view of a micro-instrument with a bending or deforming cantilever in the lid.

In the case of in-coming insonification energy, the response may consist of the changing vibration energy spectrum characteristic of a vibrating or bending sub-member such as a cantilever 202. (FIG. 2). In the case of an in-coming RF radiation signal, the response signal may be an RF or other electromagnetic signal containing the desired data transmitted from an on-board micro-instrument antenna.

Embodiments Using Mechanical Mechanisms

An isometric view of a micro-instrument 100 of one preferred embodiment is shown in FIG. 1 with a cut-out section showing a cavity or chamber 110. The micro-instrument 100 includes a base 102 and a lid 104. The base 102 has a first wall (floor) 106 that forms the floor of the micro-instrument, and a second wall 108 that circumscribes the first wall 106. The micro-instrument 100 has a cylindrical shape with a diameter d and a thickness or height t1. Other shapes may be used, such as a cube, a box, a sphere, a rod, or more complex shapes. Preferably, the thickness is less than the diameter to form a vibratable or deformable lid or plate 104 and/or 106. The diameter is preferentially between 100 microns and 1 micron or even sub-micron. For example, the micro-instrument 100 has a diameter in the range of d=30 to 0.1 microns, or preferably a diameter of d=12 to 0.5 microns. The size tolerances may be tightly controlled using industry accepted I.C. and MEMS fabrication processes. For example, d=5 microns +/−2% and t1 =1.0 microns +/−2% are achievable using the manufacturing techniques described above.

The micro-instruments 100 may also be smaller than conventional contrast agents, which typically are between 2 and 7 microns in (spherical) diameter. It is desirable to minimize the size and dosage of the micro-instrument 100 to reduce problems relating to microembolisms of the heart or brain caused by agglomeration. Unlike conventional contrast agents, these micro-instruments may have very long lifetimes and may be used with low doses since even at low doses many measurements per cubic centimeter are provided.

The lid 104 and/or base 106 may be forcibly resonated using external acoustic insonification (as might be the case during ultrasound contrast imaging). The first wall of the base 106 is circular as shown. The first wall 106 may have a resonant frequency that is lower or higher than the resonant frequency of the lid 104. For example, the thickness of the lid 104 and the first wall 106 is different. In this manner, one or more device surfaces provide an observable property that is design-tunable.

In this example of FIG. 1, the resonant frequency of the lid 104 varies as a function of temperature since the vibration is a known function of material properties (e.g., shear modulus) which are a function of temperature. The FIG. 1 device will also vary its acoustic signature as a function of blood pressure as the lid 104 bends under slowly varying blood pressure stress. Thus, an observable property of the micro-instrument 100 (e.g., resonant frequency of the lid 104) varies as a function of a physiological property (e.g., temperature or pressure). Micro-instruments 100 are "tuned" or designed to predictably respond to the physiological parameter of interest, preferably either in a monotonic or digital (off/on) manner. In general, the micro-instrument behavior that is made to correlate with the physiological property is a dynamic behavior, such as a resonant frequency, or a pseudostatic behavior, such as a state of bending (stressing) of a membrane. The response signal thereby contains information regarding the desired parameter. Because of the small size, micro-instruments rapidly respond to their environment.

The lid 104 and base 106 of a pressure sensing micro-instrument 100 with a sealed cavity 110 distorts when exposed to ambient blood pressure. In that case, the lid 104 and the base 106 may be made of single layer materials such as silicon, silicon nitride, silicon dioxide or glass.

A bimetal element or lid for temperature sensing is made of two or more layered and fused materials which deform under the influence of heat due to unequal thermal expansion. "Bimetal" herein includes materials other than metals that have differing expansion characteristics. Alternatively, bimetal materials, single layer materials or laminates may be used for either or both of the lid 104 and base 102, a cantilever 202 (FIG. 2) in the lid 104, other components, portions of components, or a single component consisting of the entire micro-instrument.

The micro-instrument 100 can include a thermally-bendable bimetal laminate material in the lid 104 and/or the base 102. Without a bimetal in micro-instrument 100 the sealed lid 104 may still bend in response to blood pressure changes. Such bending alters the vibration characteristics of lid 104 as well as the acoustic reflectance and scattering behavior in response to insonification. The micro-instrument's driven vibratory deformation is affected by the frequency of the insonification acoustic signal. The lid 104 is most easily vibrated by an insonification centered at or at least containing the resonant frequency of the lid, or one of its harmonics. This frequency is a function of any pre-existing bending (and therefore stress) caused by blood-pressure bending or by bimetallic thermal bending in the case where temperature is being monitored and a bimetal lid or base warps predictably with temperature. The acoustic scattering of the micro-instrument 100 varies as a function of the bending curved surfaces. In the case of a bimetal cantilever 202 (FIG. 2), the cantilever may bottom-out or bend against the chamber bottom at a chosen temperature. When this happens, the cantilever is no longer able to be acoustically vibrated-serving as an indicator that the chosen temperature has been reached.

The weight or density of the overall micro-instrument 100 is controlled, if desired, to make the micro-instrument 100 neutrally buoyant in a bodily fluid or tissue. In many instances, the wettability of the external surfaces along with the electro-potential, that is the zeta potential, determines whether the micro-instrument stays in suspension and does not agglomerate.

If desired, coatings or materials may be employed on selected surfaces of micro-instrument 100 to promote tissue (or bone) attachment or in-growth. The micro-instrument 100 is incorporated into the tissue itself to become permanently immobilized. Such coatings are currently used in the field of medical stents and pacemaker lead wires.

In alternative embodiments, the micro-instrument 100 has an unsealed or ruptureable compartment 110 that can hold a medical agent such as a drug. The compartment is ruptured by one or more of a variety of means including an ultrasound signal, a mechanical release mechanism, an electro-mechanical release mechanism, or other dissolving or diffusion mechanism. Once the compartment is unsealed, the medical agent is released into the surrounding fluid or tissue either all at once, or gradually as by diffusion or permeation. For example, the lid 104 is cracked or shattered by an ultrasound release pulse, or the lid 104 may be permeable to drugs to begin with and not require breakage.

Figure 3:
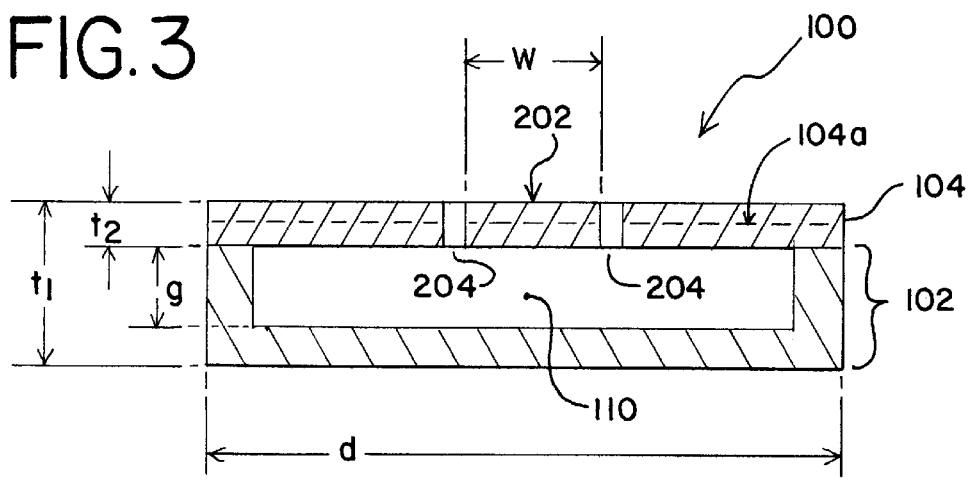
FIG. 3 is a cross-sectional view of the micro-instrument of FIG. 2.

Referring to FIG. 2, the micro-instrument 100 is illustrated in one embodiment as having a bendable cantilever 202 in the lid 104. The cantilever 202 is suspended by one end and hangs over the cavity 110 (FIG. 3). The cantilever 202 is vibrated up and down by externally applied acoustic energy. In the case of measuring temperature, the cantilever 202 preferably comprises a bimetal having a resonant frequency which is a function of temperature or by bottoming out on the interior chamber floor at a specific temperature via thermal bending. A bimetal layer for the cantilever 202 is indicated by laminate material interface 104a of FIG. 3.

The cantilever 202 has a width W, a length L and a thickness t2. The cantilever 202 is separated from the rest of the lid 104 by a gap 204. The gap 204 is preferably sufficiently small to make the cavity 110 unwettable by blood. For example, the gap 204 is 0.2 microns wide at the widest point. The cantilever bends appreciably over the range 20–50° C. and bottoms out as a function of L and G, where G is the bending distance to bottom-out. Within a population of micro-instruments L or G may vary, resulting in different devices measuring different temperature values via different bottoming temperatures.

In one embodiment, a plasma fluorine surface-treatment makes the micro-instrument surfaces unwettable (internally and/or externally). The cavity 110 remains dry and the vibrating cantilever 202 has blood on the outside and air or other gas in the cavity 110. If the gap 204 is larger and/or wettable by blood, the cantilever 202 is wetted on the exterior and interior surfaces. In an internally wettable micro-instrument 100 the bimetal cantilever 202 bends mainly in response to changing temperature as slowly-varying hydrostatic pressure is more or less equilibrated through the gap 204. Conversely, in an internally non-wettable micro-instrument 100 the cavity 110 is dry from blood constituents and the cantilever 202 is deformed by both temperature and pressure. Since blood pressure variation is approximately sinusoidal, the contribution of the temperature is represented by the constant bimetal bending offset, detectable by resonance change or by bottoming.

When measuring temperature during hyperthermia (i.e., tissue heat-treatment), the temperature range of 40–55 degrees Centigrade is of particular interest. Micro-instruments 100 that bottom out at various temperatures, such at each 0.5 degree increment, in that range are administered into the body. The first subgroup of micro-instruments 100 bottoms at 40 degrees, the second subgroup at 40.5 degrees, the third subgroup at 41.0 degrees . . . and the Nth subgroup at 55.0 degrees. Numerous identical micro-instruments 100 for each temperature increment maybe used to statistical benefit. The body temperature distribution is determined accurately in a noninvasive manner by observing the cantilever population frequency spectrum (or the absence thereof) in the acoustic signals. The micro-instruments 100 provide the temperature information that varies with local temperature changes within milliseconds. The modulus of elasticity E (and therefore frequency) of the cantilever 202 material(s) is determined and calibrated to a function of temperature.

The fundamental mechanics of a vibrating beam in air are described as follows:

$$F=(22.4/2Pi)(EIg/wL4)1/2,$$

where

E is the modulus of elasticity of the beam material

I is the moment of inertia of the beam section g is the acceleration of gravity w is the weight/unit length of the beam L is the beam length And **N means raised to the power of N Pi is pi or approximately 3.14159

See e.g., Roark and Young, "Formulas for stress and strain" McGraw-Hill.

As the temperature changes, two mechanisms in the micro-instruments respond to temperature by the bottoming out of the cantilever and/or non-boftomed cantilevers' vibration characteristics. Subsets of the micro-instruments are assigned to indicate particular temperatures relatable to temperature. By frequency analysis or amplitude measurement of the response at a location, the temperature is determined.

The micro-features, such as the sensor cantilever 202, may also vibrate at natural harmonic frequencies, sub harmonics or superharmonics of a fundamental frequency. These frequencies range from kilohertz to megahertz and depend on the designed size and stiffness of the deformable micro-feature. For example, a micro-instrument 100 arranged to have a fundamental frequency (or harmonic) of a few megahertz is excited and sensed by existing 1–10 MHz medical ultrasound imaging transducers. The observable property of the micro-instruments 100 is used, for example, to map temperature or pressure by observing the temperature or pressure dependent vibration of the cantilever's 202 harmonic or sub-harmonic frequencies or by observing when subgroups bottom-out (or both).

In alternative embodiments, the distortable sub-member, for example a cantilever 202, a diaphragm, a membrane, or other flexural member(s), is contained entirely within the cavity 110 such that the distortable member is not in direct contact with the external bodily fluid or tissue. Thus, the cantilever 202 is housed within the sealed cavity 110 of FIG. 1 and mounted to the interior of the cavity 110. The motion of an isolated internal cantilever 202 is mechanically transmitted to the surrounding blood and tissue through the walls of the micro-instrument 100. This configuration avoids wetting the cantilever 202 and vibration-damping thereof by blood.

Referring to FIG. 3, a cross-sectional view of the micro-instrument 100 of FIG. 2 is shown. The thickness of the cantilever 202 is different from or the same as the thickness of the rest of the lid 104 and/or from the thickness of the base 102. A variable thickness cantilever (or membrane) cross-section may be used to enable more than one vibrational mode or frequency to be excited.

Embodiments Using Electrical Mechanisms

Figure 4:
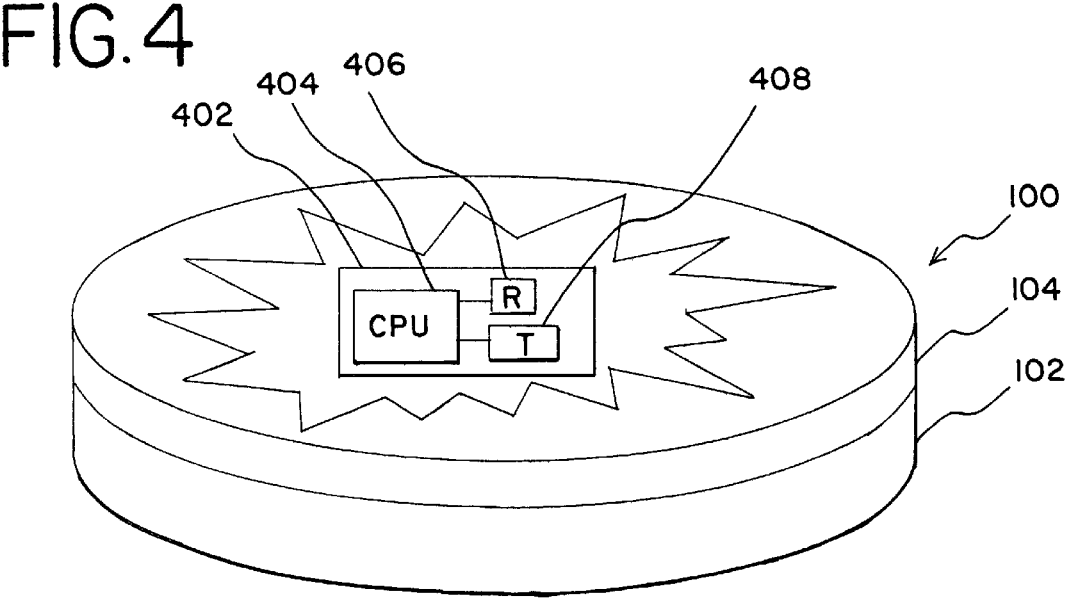
FIG. 4 is an isometric view of a micro-instrument with a cut-out showing an electronic circuit attached or integrated into a micro device.
Figure 5:
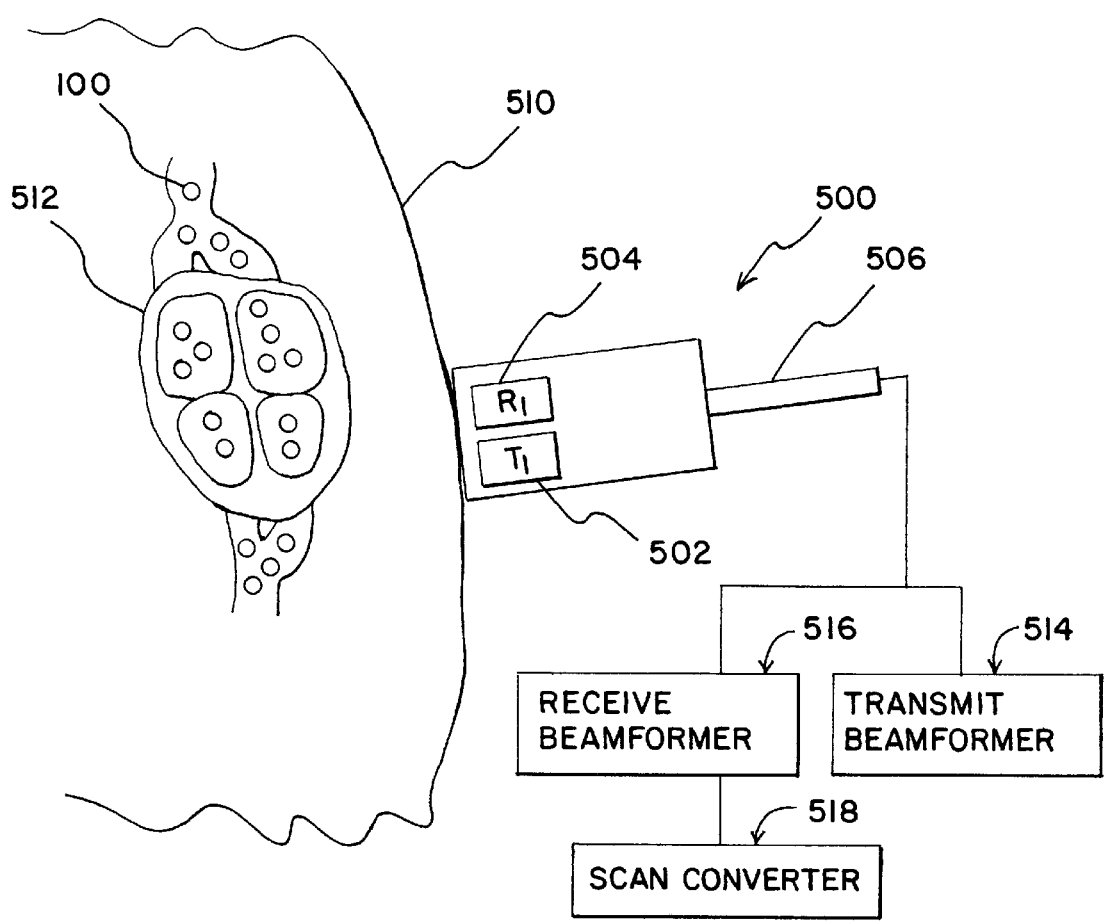
FIG. 5 is a view of a transducer probe and a section of a body containing the heart.

As discussed above, the micro-instrument in one embodiment includes an electrical device such as an electrical sensor for at least one of generating the observable characteristic or influencing the observable characteristic as a function of a physiological property. FIG. 4 shows a micro-instrument electronic circuit 402. The electronic circuit 402 includes a micro-instrument receiver 406, a micro-instrument transmitter 408, and a micro-instrument processing, logic and/or memory unit 404. The receiver 406 in the micro-instrument 100 receives initiation signals from an external transmitter 502 (FIG. 5). The external transmitter 502 may send one or both of an acoustic signal or an electromagnetic signal to initiate data retrieval from micro-instruments 100. In the case of an electromagnetic signal, the receiver R is an electromagnetic receiver coupled to a micro-instrument 100 antenna. Such a transmitter/receiver is an RF or other frequency-range system.

Using known identification-tag technology, power may be provided to the micro-instrument 100 through the micro-instrument antenna. The transmitter 408 of the micro-instrument transmits electromagnetic response signals to an external receiver 504 (FIG. 5) of the probe 500, in the case in which that signal is electronic as opposed to acoustic. The micro-instrument 100 generates the response signal as a function of a body parameter, such as temperature.

The electronic circuit 402 integrates with the micro-instrument 100 on the exterior surface, interior surface, or in the base 102 or lid 104. The parameter of interest may alternatively be measured without electromagnetic signals, such as where the micro-instruments 100 receive an acoustic transmission and the temperature information is detected from returned acoustics, such as reradiated acoustics.

The use of an electronic circuit 402 that includes components such as a stress-sensing piezoresistor array increases the accuracy and functionality of the micro-instrument 100. In one embodiment, a piezoresistor array includes a diffused electrical resistor array or a Wheatstone Bridge. The characteristic electrical resistance of an integrated piezoresistor array is related to stress on the micro-instrument 100. The piezoresistor array is located in the flexural structure of micro-instrument 100. Flexure due to vibration, static distortion, or bimetallic bending modulates the resistance. Stress is monotonically related to pressure and thus monotonically related to deformation or flexing of the lid 104. Thus, electrical resistance of a resistor network in the electronic circuit 402 is related to the blood pressure causing flexing of the micro-instrument 100.

In one embodiment, the electronic circuit 402 includes, in addition or instead of a pressure sensor, a temperature sensor. The temperature sensor may be a thin-film or diffused thermocouple, thermistor, temperature-sensitive diode or other temperature sensitive device. The temperature, as measured by the temperature sensor within micro-instrument 100 may also be used for correcting undesired temperature dependencies of a resistive pressure sensing network. Also, the temperature may be used both for determining the ambient temperature and corrected pressure in the area around the micro-instrument 100.

The electronic circuitry 402 may include one or more of various electrical circuits, such as: an analog to digital converter("A/D"), a digital to analog converter("D/A"), a power converter, memory, trimming resistors, fuses, programmable links, programmable gates, compensation circuitry, calibration circuitry, biasing circuitry, transistors, transmitters, receivers or signal-processing circuitry. Thousands of sub-micron transistors can be integrated in the external and internal surfaces of the micro-instrument 100. The electronic circuits 402 may also be laminated (e.g. by thin-film deposition) inside of the micro-instrument 100 layers. High density sub-micron memories have been created by Irvine Sensors of Irvine, Calif. for DARPA in that manner.

In one embodiment, a thin-film spiral RF antenna, such as Spiral RF antennas used with radio frequency (RF) communication and identity-tag devices, are formed on or in the interior or exterior of the micro-instrument 100. The antenna receives radiated RF energy to power the electronic circuit 402. The same antenna may be used to transmit and receive signals, including response signals that contain temperature or pressure information.

As the micro-instruments 100 become smaller, the antenna also becomes smaller. Smaller antennas use higher frequencies. Communication frequencies are preferably in the microwave, RF, terahertz, or Gigahertz range.

In one alternative or additional embodiment, the electronic circuit 402 includes an energy source, such as a thin-film battery. The battery preferably includes a multi-laminate interdigitated thin-film cell. Alternatively, electrolytic or galvanic electrodes on the exterior surfaces of the micro-instrument 100 are provided. Such electrodes, when immersed in the blood or other electrolyte, create a slight current by an electrolytic action. In this manner long-lasting power is made available.

Any power source may also provide an offset voltage, calibration voltage, current or other voltage bias to the electronic circuit 402. The electronic circuit 402 uses such voltages, for example, to compensate for unwanted offsets in the pressure or temperature measurements.

When the electronic circuitry 402 includes a memory, the memory may record the readings of the parameter measurements. These measurements are used in later calculation, comparison, or are transmitted at a later time. The memory may also store individual micro-instrument identity information or executable commands.

Figure 6:
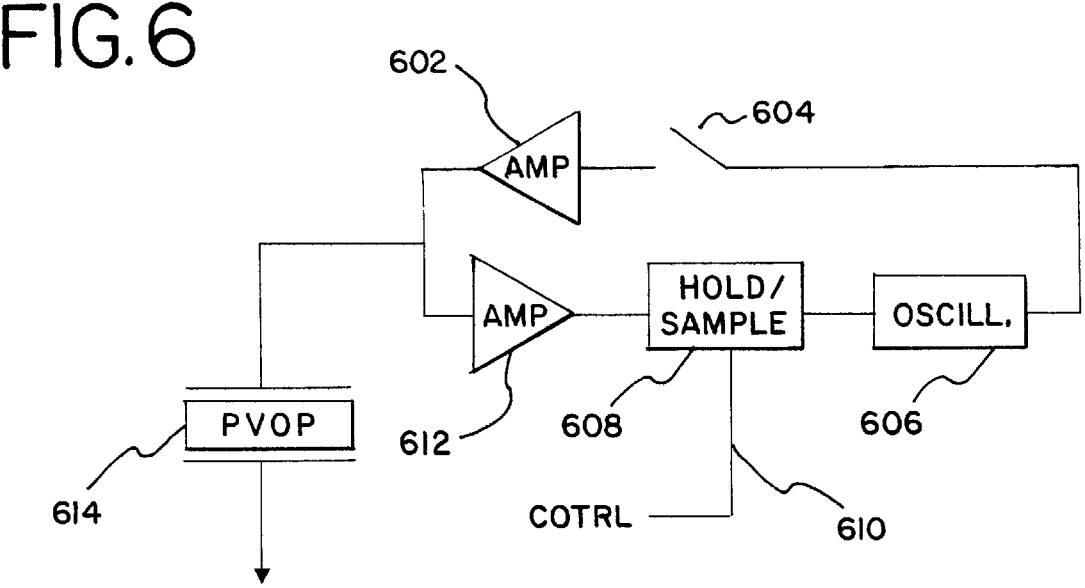
FIG. 6 is an electronic circuit diagram suitable for use in the micro-instrument of FIG. 4.

Referring to FIG. 6, an example of one possible embodiment of the electronic circuit 402 (FIG. 4) is illustrated. The electronic circuit 402 includes a poly-vinylidene flouride ("PVDF") component 614 connected to ground, a first amplifier 602 connecting a switch 604, which is controlled by a control signal to the PVDF component 614 and a second amplifier 612, the second amplifier 612 is connected to a sample and hold circuit 608, which is controlled by control signal 610, and a voltage controlled oscillator 606 connected to the sample and hold circuit 608 and the switch 604.

The PVDF component 614 senses blood pressure and generates a signal, for example an omni-directional ultrasound signal, on demand as a function of the blood pressure. Imaging Referring to FIG. 5, a section of a living body 510 is shown with a heart 512 and a plurality of micro-instruments 100 in the blood stream and the heart. A probe 500 is placed against the body 510. The ultrasonic imaging probe 500 includes a cable 506, a transmitter 502, and a receiver 504. The transmitter 502 emits an acoustic signal into the body. The receiver 504 receives a response signal from the micro-instruments 100. The transmitter 502 and receiver 504 are the same or different devices, such as an array of piezo-electric elements. The piezo-element(s) may also form the ultrasound imaging array or may be independent from the array. Alternatively, the micro-instrument 100 can generate the response signal without receiving an acoustic signal. That is, the micro-instrument 100 automatically transmits. In alternative embodiments, the transmitter and receivers are electromagnetic in nature for MRI, CAT scan, PET, optical, x-ray or other imaging.

The probe 500 is coupled with an ultrasound imaging system via cable 506. As shown, transmit and receive beamformers 514 and 516 are coupled with the cable 506. The transmit beamformer 514 comprises any device for generating transmit waveforms, such as the transmit beamformer disclosed in U.S. Pat. No. 5,675,554, the disclosure of which is herein incorporated by reference. The transmit beamformer 514 generates transmit waveforms that are applied to the transmitter 502. In response, the transmitter 502 transmit acoustic energy into the body.

The receive beamformer 516 comprises any device for summing signals responsive to acoustic echoes to form data representing a line through the body 510, such as the receive beamformer disclosed in U.S. Pat. No. 5,685,308, the disclosure of which is herein incorporated by reference. The receive beamformer 516 receives an electrical signal from each of the elements of the receiver 504. The signals are summed.

The output of the receive beamformer 516 is electrically connected with a scan converter 518. The scan converter comprises devices for detecting and formatting the data for display as an image. Any of various ultrasound systems may be used, such as the Acuson ultrasound systems with the tradenames 128XP, Aspen or Sequoia, or ultrasound systems made by other manufacturers. In alternative embodiments, the probe 500, transmitter 502, receiver 504, transmit and receive beamformers 514 and 516 and/or scan converter 518 comprise devices for CRT, MRI or CAT scan imaging. The receiver 504 and transmitter 502 are conveniently located in transducer 500, but may be located elsewhere in the system.

For imaging, a single micro-instrument 100 or hundreds or more of the micro-instruments 100 are administered or placed within the body 510. The micro-instruments 100 may conveniently be injected, as are conventional contrast agents, into the bloodstream. For example, the micro-instruments 100 are suspended in conventional solutions of saline and wetting agents as desired. In alternative embodiments, the micro-instruments 100 are administered in any other acceptable manner including propelling into tissue, swallowing, inhalation, urethraly, annally or using a needle. For example, when prostate cancer is treated by hyperthermia microwave treatment, the micro-instruments 100 are injected directly into the prostate gland and the surrounding tissues, preferably using a hollow needle.

The density of micro-instruments 100 is less than, the same as, or greater than the density of conventional contrast agents. The density of micro-instruments 100 in a portion of the body is preferably between 1 and $1 \times 10^{+9}$ micro-instruments per cubic centimeter. To measure pressure with a resolution of 1 mm in 3 dimensions, micro-instrument density can be on the order of only 1,000 micro-instruments per cubic centimeter, several orders of magnitude lower than for conventional agents.

The probe 500 acoustically excites the micro-instruments 100 and receives an acoustic response signal. The response signal may include reflected, absorbed or scattered ultrasound energy that is indicative of the induced state of vibration or distortion. The state of vibration in one embodiment is modified by the micro-instrument 100 as a function of the physiological property. Thus, acoustic energy returning from the micro-instruments 100 is used for one or both of acoustic contrast imaging of tissue/blood and/or mapping of a body parameter such as temperature or pressure. In alternative embodiments, other signals from the micro-instrument 100 are used for mapping the body parameter.

The micro-instruments may be used for purposes other than mapping a body parameter. In medical ultrasound imaging it is often desirable to correct aberration. The distortion and defocus effects of acoustic velocity gradients in tissues are eliminated or reduced to generate a more precise image. Numerous micro-instruments 100 each generating a different identification signal, may be used to correct such aberration. For example, the electronic circuit 402 broadcasts a different identification signal for each such micro-instrument 100. The identification signals are useful to correct acoustic aberration. The location of one or more uniquely identified micro-instruments is used to correct the image. Such corrections are performed in real-time or via post-processing.

In one embodiment, the micro-instrument 100 acts as an acoustically imageable contrast agent. In addition to imaging from echoes reflected from the micro-instrument 100 the signal generated by the micro-instrument 100 representing a physiological parameter is received by the probe 500 and processed to form an diagnostic image conveniently containing both ultrasound tissue and/or blood image information and the mapped parameter (e.g. temp, pres.) information.

For this embodiment, the micro-instrument may also include electrical mechanisms. The micro-instrument 100 transmitter 408 continuously, periodically or responsively transmits parameter information. The continuous transmission mode may be triggered by an initiation signal such as a pulse at a certain frequency. The transmitted information can be frequency modulated or frequency encoded. For example, for a transmitted acoustic signal a shift from 2 MHz to 2.1 MHz may indicate a pressure increase of 1 mm of mercury. This could also be true in the case of a transmitted RF signal.

Three embodiments of the micro-instrument 100 for imaging are described below for illustration purposes:

First, a temperature measurement and mapping configuration includes a micro-instrument 100 with a bimetallic (or laminate) cantilever 202 that distorts as a function of local temperature. Numerous micro-instruments 100 with such cantilevers 202 that bottom-out at various known but different temperatures are administered into the living body 510. Optionally, the cantilever 202 is surrounded by hydrostatically pressure-equilibrated body fluid providing a micro-instrument 100 with a bimetal cantilever and an internally wettable chamber 110. By varying the lithography patterns when creating the different micro-instruments 100, various resonant frequencies and associated bottom-out temperatures are created. Temperature is mapped in the acoustic imaging field of view as a function of the observable acoustic response of the micro-instruments. The temperature information is communicated acoustically via the progressive loss of portions of the acoustic response spectra corresponding to bottomed-out microinstruments.

Second, a temperature measurement configuration alternatively includes a bimetal micro-instrument 100 without a cavity 110. The lid 104 is made of a first material or property and the base 102 is made of a second different material or property. The first and second materials or properties have different coefficients of thermal expansion, such as two different bimetals. This micro-instrument 100 is substantially disc shaped and solid. The lid 104 and base 102 have the same or different thickness. As the temperature changes, the multilayer micro-instrument 100 thermally warps such that, at least at one insonification frequency, resonant vibration properties change or acoustic scattering changes. For example, the micro-instrument 100 deforms into the shape of a bowl or dish, changing its resonant frequency to a higher value. The deformed micro-instrument 100 also reflects or scatters high frequency insonification signals differently. Again, the micro-instruments 100 permit mapping temperature in the acoustic imaging field of view. The acoustic response is indicative of temperature.

Third, a pressure measurement configuration includes a micro-instrument 100 with a cavity 110, but without bimetallic materials in the lid 102 or the base 102. The base 102 and the lid 104 are made of the same material and are both pressure-deformable. When the pressure increases, the lid 104 and base 102 deform inwardly and may be designed to bottom out against each other at a known pressure. When the lid 104 and the base 102 bottom out, the micro-instrument 100 vibrates in a reduced-amplitude manner as a coupled diaphragm. This progressive transition is indicative of pressure. Numerous micro-instruments 100 can be administered into the body 510 with different bottom-out pressures and different resonant frequencies. The resonant frequencies are selected such that the micro-instruments 100 bottom out and alter acoustical response at a particular frequency as a function of a certain pressure. The pressure change may preferably be determined from observing how the micro-instrument 100 population stops responding in a particular frequency (pressure) range. For example, by varying the diameter of the cavity 110 among the micro-instruments 100 the resonant frequency and bottom-out pressure are both changed consistently via a simple lithography mask variation.

Referring to Table 1, a summary of various embodiments is provided. Table 1 lists some options for what physiological parameters can be measured, how a communication of said parameter(s) may be powered, how the parameter is sensed on the micro-instrument(s), 100 how the parameter communication may take place and finally, how different parameter values or states can be differentiated.

It is expected that a wide variety of sensors will be employed for a wide variety of purposes. It is not the purpose here to review the vast and growing literature on silicon or thin-film based chemical sensors, or other sensors. The point is that our novel micro-instrument approach is ideally suited to incorporate all such sensors.

TABLE 1

| Some example parameters that may be measured by micro-instruments | Temperature, pressure, ionizing dose, drug concentration, presence of chemical or molecular species (e.g. bacteria, virus, blood sugar protein, genetic constituents) |
| Some example methods for providing power to transmit the parameter | External acoustic illumination<br>External RF illumination<br>External microwave or electromagnetic |

TABLE 1-continued

| signal from micro-instrument | illumination<br>On-board thin-film solid-state battery<br>On-board thin-film electrodes form battery with body fluid |
| Some example methods for sensing parameter on micro-instruments | Changing acoustic behavior of flexural features<br>Changing electrical signal from a thermocouple, thermistor, diode, resistor bridge<br>Changing electrical signal from a piezofilm such as PVDF, PZT or ZnO |
| Some example methods for communicating parameter from micro-instrument | Passively, as by analyzing returned, scattered or reflected illumination energy<br>Actively, as by RF signal powered by on-board electrochemical battery<br>Semi-actively, as by illumination (to provide power) and subsequent RF transmission<br>Semi-actively, as by acoustic illumination of micro-instrument and generation by that micro-instrument of frequency-encoded pressure information |
| Some example methods for differentiating parameter values | Frequency encoding on each micro-instrument-such as (a) flexural members which behave as a function of the physiological parameter, b) an on-board RF or acoustic transmission which is frequency-encoded or digitally encoded. |

Other microstructures incorporated into a micro-instrument 100 that goes through either a gradual or threshold change in behavior with temperature or pressure or any other body parameter may be used. The micro-instrument 100 described above utilizes flexural submembers or portions whose acoustic behavior changes with temperature or pressure (the parameter of interest)—and this acoustic change is observed using an insonifying imaging (or other) transducer. We have also described a temperature measurement micro-instrument of the type in FIG. 4 wherein a thermistor or thermocouple communicates via an RF link. Similar pressure or temperature micro-instruments 100 having no flexural parts may be used.

Figure 7:
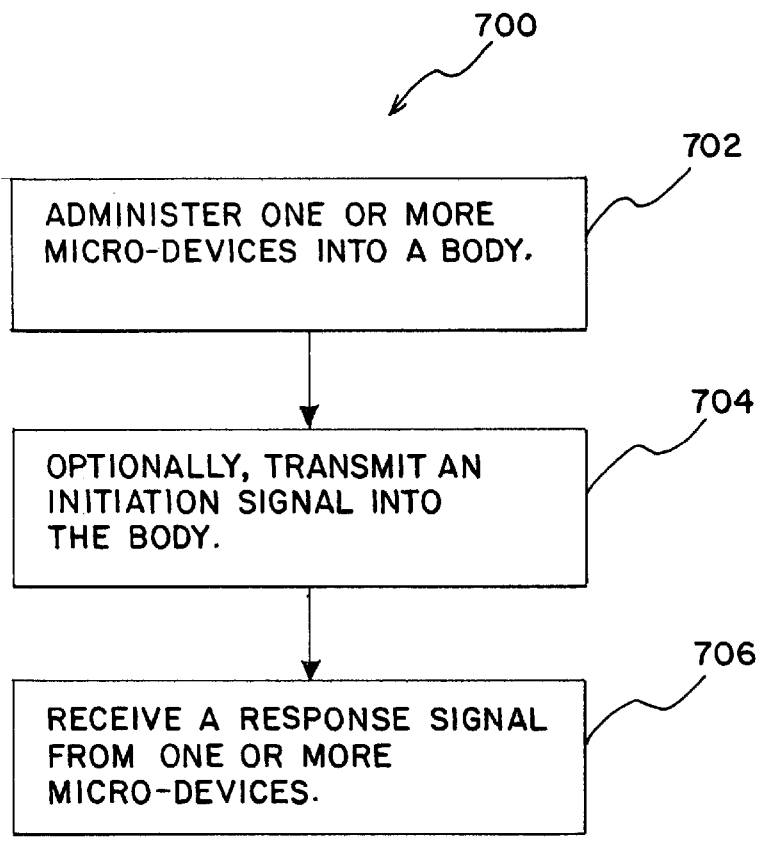
FIG. 7 is a flow diagram of a method for using the micro-instrument of FIGS. 1–4.

Referring to FIG. 7, one embodiment of a method 700 of medical diagnostic information gathering 700 includes the steps of administering 702, transmitting 704, and receiving 706. The method of FIG. 7 is used, for example, to determine pressure distribution in the body 510. First, a plurality of micro-instruments 100 are administered at 702 into the body 510.

Second, an optional initiation signal is transmitted into the body at 704. The initiation signal is generated external to the body 510 or by another micro-instrument 100 catheter or other device in the body 510. Then, at least one response signal from at least one of the plurality of micro-instruments is received at 706. The response signal is preferably received external to the body 510, but may be received by a device within the body 510. The response signal varies as a function of a characteristic of a portion of the body near the micro-instrument 100 in this case pressure. If an initiation signal is not transmitted, then the signal generated in step 706 may be automatically generated.

In one embodiment, the observable property of a first group of micro-instruments 100 and a second (or Nth) group of micro-instruments 100 undergoes a threshold transition such as bottoming out at respective temperature value for each subgroup.

Referring to FIG. 8, one example of a method for using micro-instruments for treatment is shown. The method 900 generates thermal energy in a body to kill cancerous cells and monitors the temperature distribution during that therapy.

At 902, a plurality of the micro-instruments are administered into a body. Preferably, each micro-instruments is less than one millimeter in each dimension. At 904, a first initiation signal is transmitted into the body.

At 906, an observable property that indicates a temperature at the micro-instrument 100 is communicated external to the body. The communication is responsive to the first initiation signal 904.

At 908 the hyperthermia device (e.g., transducer, microwave horn, RF antenna etc) delivers an increment of heat to the tissue. The steps 906 and 908 are repeated until the required thermal dose is delivered at step 910.

The method of FIG. 8 can be used to target organs or cells, such as cancer cells. The cells are destroyed by the thermal energy. The method of FIG. 8 can most beneficially be used in conjunction with volumetric thermal mapping of the body 510.

In one embodiment, the micro-instrument particles are active acoustic transmitters that are synchronized to the receive beamforming of an ultrasound system via a high frequency radio signal transmitted trigger. In this configuration, the ultrasound property mapping subsystem is in receive-only mode. The particles generate ultrasonic energy indicating pressure or temperature, such as by frequency encoding. The ultrasound system generates a property image in response to the energy. Transmission of acoustic energy from the ultrasound system for conventional imaging may be interleaved with reception of energy originally generated from the micro-instruments 100.

A short period of time before the scanner begins receive-beamforming, an RF trigger signal is generated. The micro-instruments 100 upon reception of the trigger signal, latch a pressure or temperature sensed signal and, using a voltage controlled oscillator, resonate an embedded element or cantilever at a frequency that is equivalent to a measured pressure (i.e. low pressure=2 MHz, high pressure=4 MHz). Preferably, a short cycle burst (e.g. 10 cycles) is used. This burst is received and beamformed by the scanner to the proper depth and area within the image plane. The arrangement of FIG. 6 allows the PVDF elements to both sense pressure and acoustically transmit information indicating the pressure value.

In any of the frequency encoded embodiments discussed above, the system applies a short, windowed FFT across the received ultrasound beam broad band signal to encode for center frequency.

While preferred embodiments have been shown and described, it will be understood that they are not intended to limit the disclosure, but rather it is intended to cover all modifications and alternative methods and apparatuses falling within the spirit and scope of the invention as defined in the appended claims or their equivalents.

What is claimed is:

1. A micro-mechanical device for admission into a body and for communicating medical diagnostic information, comprising:

a leadless micro-instrument particle having an observable property that varies as a function of a physiological property;

said micro-instrument having a maximum dimension of one millimeter and a cantilever on a surface of the micro-instrument particle, the cantilever operable to generate the observable property as an acoustic signal.

2. The device of claim 1 wherein the observable property comprises a property observable in a modality selected from the group consisting of: ultrasound, magnetic resonance, computerized axial tomography, PET, x-rays and optical imaging.

3. The device of claim 1 wherein the micro-instrument particle comprises a particle shaped as a function of lithography and at least one of deposition and etching.

4. The device of claim 1 wherein the micro-instrument particle comprises a material selected from the group consisting of: silicon, oxides of silicon, nitrides of silicon, metallic thinfilms, ceramic, glass and combinations thereof.

5. The device of claim 1 wherein the observable property varies as a function of a temperature in a body.

6. The device of claim 1 wherein the observable property varies as a function of a pressure in a body.

7. The device of claim 1 wherein the cantilever is responsive to the physiological property.

8. The device of claim 1 wherein the micro-machine particle comprises a solid state sensor operative to sense the physiological property.

9. The device of claim 1 wherein the observable property comprises an acoustic response characteristic.

10. The device of claim 1 wherein the observable property comprises electromagnetic information.

11. The device of claim 1 wherein the observable property comprises optical information.

12. The device of claim 1 wherein the micro-instrument particle comprises:

a structure comprising a base, a lid connected with the base to form a cavity and the cantilever on at least one of the lid and base.

13. The device of claim 1 wherein the micro-instrument particle is less than twenty-five microns in each dimension.

14. A medical diagnostic ultrasound system for observing a physiological property of a body, the system comprising:

a transducer operable to transmit energy into the body;

a plurality of micro-instrument particles having an observable property responsive to the ultrasonic energy, the observable property varying as a function of the physiological property of the body; and a receive beamformer operable to receive signals responsive to the micro-instrument particles along a scan line.

15. The system of claim 14 wherein the transmitted energy comprises ultrasonic energy and the observable property comprises an acoustic response to the ultrasonic energy.

16. The system of claim 14 wherein the observable property comprises an electromagnetic response.

17. The system of claim 14 wherein the plurality of micro-instrument particles each comprise a particle shaped as a function of lithography and at least one of deposition and etching.

18. The system of claim 14 wherein the plurality of micro-instrument particles each comprise a material selected from the group consisting of: silicon, oxides of silicon, nitrides of silicon, metallic thin films, ceramic, glass and combinations thereof.

19. The system of claim 14 wherein the observable property varies as a function of temperature.

20. The system of claim 14 wherein the observable property varies as a function of pressure.

21. The system of claim 14 wherein the plurality of micro-instrument particles each comprise a deformable member, the deformation responsive to the physiological property.

22. The system of claim 14 wherein the plurality of micro-instrument particles each comprise a solid state sensor capable of sensing the physiological property.

23. The system of claim 14 wherein the plurality of micro-instrument particles each comprise:

a structure comprising a base, a lid connected with the base to form a cavity and at least a portion of at least one of the lid and base being deformable.

24. The system of claim 14 wherein the plurality of micro-instrument particles are each less than twenty-five microns in each dimension.

25. A medical diagnostic method for gathering information representing a physiological property of a body, the method comprising the steps of:
  (a) administering at least one micro-instrument particles into the body, at least one of said particles responsive to an initiation signal;
  (b) generating an initiation signal; and
  (c) generating in response to the initiation signal an observable property signal from at least one micro-instrument particle that varies as a function of a physiological property of the body;
  (d) receiving signal information responsive to the observable property external to the body; and
  (e) generating a property or map image as a function of the information.

26. The method of claim 25 wherein (b) comprises transmitting an ultrasound signal and (c) comprises generating an observable acoustical property signal in response to the ultrasound signal.

27. The method of claim 26 wherein (c) comprises generating the observable acoustical property signal by vibrating a deformable portion of at least one micro-instrument particle.

28. The method of claim 25 wherein (c) comprises generating the observable signal in response to a temperature property of the body.

29. The method of claim 25 wherein (c) comprises generating the observable signal in response to a pressure property of the body.

30. The method of claim 25 further comprising:
  (f) administering medically diagnostic or therapeutic agent or drug from at least one micro-instrument particle as a function of the physiological property.

31. The method of claim 30 wherein (f) comprises rupturing a compartment of the micro-instrument particle.

32. The method of claim 25 wherein (c) comprises generating an observable electromagnetic property signal.

33. The method of claim 25 further comprising:
  (f) sensing the physiological property with a solid-state sensor integrated in at least one of said micro-instrument particles.

34. The method of claim 25 wherein the observable property signal of some of the micro-instrument particles varies as a function of a first value of the physiological property and the observable property of others of the micro-instrument particles varies as a function of a second, different value of the physiological property.

35. The method of claim 33 wherein (c) includes transmitting an unique identification signal from each micro-instrument particle.

36. The method of claim 25 wherein the image comprises a temperature map of a portion of the body.

37. The method of claim 25 wherein the image comprises a pressure map of a portion of the body.

38. The method of claim 25 further comprising:
  (f) correcting (b) for aberration as a function of the information.

39. The method of claim 25 wherein:
  the observable property is temperature and a temperature map is generated in support of a thermal therapy.

40. A micro-mechanical device for admission into a body and for communicating medical diagnostic information, comprising:
  a leadless micro-instrument particle having an observable property that varies as a function of a physiological property, the observable property consisting of a property selected from the group of: harmonic frequency of a signal, amplitude of a plurality of signals, on-off output operation and combinations thereof;
  said micro-instrument having a maximum dimension of one millimeter.

* * * * *